United States Patent [19]

Schröck et al.

[11] Patent Number: 5,998,650

[45] Date of Patent: Dec. 7, 1999

[54] ORGANOSILICON COMPOUNDS WITH AMINO-ALKYLENE OXIDE FUNCTIONAL GROUPS AND THEIR PREPARATION AND USE

[75] Inventors: Robert Schröck, Altötting; Thomas Hierstetter; Jochen Dauth, both of Burghausen, all of Germany

[73] Assignee: Wacker-Chemie GmbH, Munich, Germany

[21] Appl. No.: 09/195,116

[22] Filed: Nov. 18, 1998

[30] Foreign Application Priority Data

Dec. 5, 1997 [DE] Germany ............................ 197 54 038

[51] Int. Cl.$^6$ ............................................. C07F 7/10
[52] U.S. Cl. ............................................. 556/423; 528/15
[58] Field of Search ................................ 556/423; 528/15

[56] References Cited

U.S. PATENT DOCUMENTS

| | | |
|---|---|---|
| 3,032,577 | 5/1962 | Morehouse et al. . |
| 5,118,777 | 6/1992 | Okawa ..................................... 528/34 |
| 5,132,443 | 7/1992 | Traver et al. ............................ 556/425 |
| 5,164,522 | 11/1992 | McCarthy et al. . |
| 5,276,123 | 1/1994 | King et al. ............................... 556/425 |
| 5,486,634 | 1/1996 | Hahn et al. . |
| 5,591,818 | 1/1997 | Standke et al. ............................ 528/38 |
| 5,840,951 | 11/1998 | Hierstetter et al. ...................... 556/425 |

FOREIGN PATENT DOCUMENTS

| | | |
|---|---|---|
| 0 342 518 | 5/1989 | European Pat. Off. . |
| 43 44 082 | 12/1994 | Germany . |
| 43 44 082 C1 | 12/1994 | Germany . |
| 6-220200 | 8/1994 | Japan . |

OTHER PUBLICATIONS

Patent Abstracts of Japan, vol. 018, No. 591, Nov. 11, 1994 and Japan 06 220200, Toshiba Silicone Co., Ltd.
Hochmolekularbericht 1988, Toshiba Silicone KK, JA. 62 181320, 02/05/86/08/08/87 (23 484) 37.
K. Adrianov, Izv. Akad. Nauk.SSSR, Ser. Khim, issue No. 2, 351–356 (1986).
Du, ZuodongYu, Jing, Hecheng Xiangjiao Gongye, 9(6), 388–92.

*Primary Examiner*—Paul F. Shaver
*Attorney, Agent, or Firm*—Brooks & Kushman P.C.

[57] ABSTRACT

Organosilicon compounds with amino-alkylene oxide functional groups containing amino groups are disclosed.

9 Claims, No Drawings

ORGANOSILICON COMPOUNDS WITH AMINO-ALKYLENE OXIDE FUNCTIONAL GROUPS AND THEIR PREPARATION AND USE

TECHNICAL FIELD

The invention relates to organosilicon compounds with amino-alkylene oxide functional groups and their preparation and use.

BACKGROUND ART

The publication by K. Andrianov Izv, Akad. Nauk. SSSR, Ser. Khim, Volume 2, 351–356 (1968) describes the reaction of isopropyldiallylamine or triallylamine and 1,3-dihydrotetramethyldisilazane or 1,3-dihydrotetramethyldisiloxane by means of hydrosilylation. In this reaction, the reactants are used in a molar ratio of at least 2:1 to about 5:1, based on the 1,3-dihydrotetramethyldisilazane or 1,3-dihydrotetramethyldisiloxane and isopropyldiallylamine or triallylamine employed. The 1,3-dihydrotetramethyldisilazane or 1,3-dihydrotetramethyldisiloxane employed reacts to a relatively small amount (26–44%), and in each case, only once with the isopropyldiallylamine or triallylamine used. For example, in the reaction of triallylamine with 1,3-dihydrotetramethyldisiloxane, tris-[3-(1',1',3',3'-tetramethyldisiloxy)propyl]amine is obtained in only a 21% yield as the sole compound which can be isolated, and contains no allyl groups, but still contains Si-bonded hydrogen.

The publication by Du, Zuodong and Yu, Jing, Hecheng Xiangjiao Gongye 9(6), 388–92 (1986) describes silicone rubbers with N,N-bisallyl-γ-aminopropyl side chains. Their synthesis proceeds via a hydrosilylation of the monofunctional heptamethylcyclotetrasiloxane with triallylamine to give heptamethyl-N,N-bisallyl-γ-aminopropyl-cyclotetrasiloxane, which is reacted by ring opening to give the corresponding polymer (silicone rubber). This is a reaction between the molecular and monofunctional heptamethylcyclotetrasiloxane unit with a further molecular unit, the triallylamine, without the risk of a crosslinking reaction or a build-up of a chain. The synthesis of the silicone rubber takes place as a two-stage reaction via the roundabout route of hydrosilylation of the triallylamine on heptamethylcyclotetrasiloxane.

EP 342 518 B1 (published Nov. 30, 1994, General Electric Co.) describes a process for the preparation of nitrogen-silicon compounds which are obtained by hydrosilylation of an olefinic amine by polydiorganosiloxanes containing Si—H functional groups. Monoallylamines are employed as the amine components.

JP-A 06220200 (published on Aug. 9, 1994; Toshiba Silikon AG) describes organopolysiloxanes with an N-polyoxyalkyleneaminoalkyl group, in which in each case two polyoxyalkylene radicals are bonded to a nitrogen atom.

DE 43 44 082 C1 (published on Dec. 22, 1994, Th. Goldschmidt AG) describes a process for the preparation of organopolysiloxanes with secondary aminoalkyl groups bonded to silicon via carbon. In this process, secondary aminoalkenes which contain only one double bond per molecule are added onto organosilicon compounds which carry Si—H groups by means of hydrosilylation under platinum catalysis. The resulting organopolysiloxanes with secondary aminoalkyl groups bonded to silicon via carbon can then be equilibrated, if appropriate, for example with cyclic polyorganosiloxanes.

DESCRIPTION OF THE PREFERRED EMBODIMENTS

The invention relates to organosilicon compounds with amino-alkylene oxide functional groups containing a) siloxane units of the formula

in which

R are each identical or different hydrocarbon radicals having 1 to 200 carbon atoms, which are optionally substituted by halogen atoms or alkoxy or hydroxyl groups and can be interrupted by one or more oxygen atoms, $R^1$ are each identical or different alkyl radicals having 1 to 8 carbon atoms, which can be interrupted by one or more oxygen atoms, a is 0, 1, 2 or 3 and b is 0, 1, 2 or 3, with the proviso that the sum $a+b \leq 3$, and b) per molecule, at least one unit of the formula

and at least one unit of the formula

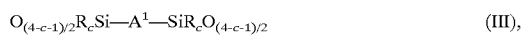

in which

R can each be identical or different and has one of the abovementioned meanings, c can be identical or different and is 0, 1 or 2, preferably 2, A is a radical of the formula

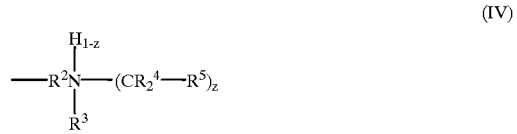

and $A^1$ is a radical of the formula

in which $R^2$ can each be identical or different and is a divalent hydrocarbon radical having 2 to 12 carbon atoms, $R^3$ can each be identical or different and is a radical of the general formula

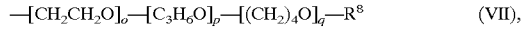

in which $R^8$ is a hydrogen atom, an alkyl radical having 1 to 22 carbon atoms, a group of the formula $-SiR_x(OR^1)_y$, in which R and $R^1$ can be identical or different and have one of the abovementioned meanings and x and y independently of one another are 0, 1, 2 or 3, with the proviso that x+y equals 3, or is a radical of the formula $-CO-R^9$, where $R^9$ is an alkyl radical having 1 to 8 carbon atoms, z is 0 or 1, preferably 1, and o, p and q independently of one another are 0 or an integer from 1 to 200, preferably 0 or an integer from 1 to 35, with the proviso that the sum o+p+q>0, $R^4$ is identical or different and is a hydrogen atom or an alkyl radical having 1 to 8 carbon atoms and $R^5$ is a hydrogen atom or a radical of the formulae —$CR^6$=$CR^6{}_2$ or —C≡$CR^6$, in which $R^6$ can be identical or different and is a hydrogen atom or an alkyl radical having 1 to 8 carbon atoms.

The organosilicon compounds according to the invention preferably contain no further units apart from the units of the formulae (I), (II) and (III).

The organosilicon compounds according to the invention preferably have an average molecular weight of 500 to 1,000,000 g/mol, particularly preferably 5000 to 150,000 g/mol, and preferably a viscosity of 10 to 15,000,000 mm²/s, particularly preferably 20 to 100,000 mm²/s, in each case at 25° C.

The organosilicon compounds according to the invention have an amine number of preferably 0.003 to 6, the amine number corresponding to the number of ml of 1N HCl required for neutralization of 1 g of substance.

Examples of R are alkyl radicals, such as the methyl, ethyl, n-propyl, iso-propyl, 1-n-butyl, 2-n-butyl, iso-butyl, tert-butyl, n-pentyl, iso-pentyl, neo-pentyl and tert-pentyl radicals; hexyl radicals such as the n-hexyl radical; heptyl radical, such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl and cycloheptyl, and methylcyclohexyl radicals; aryl radicals such as the phenyl, naphthyl, anthryl and phenanthryl radicals; alkaryl radicals, such as o-, m- and p-tolyl radicals, xylyl radicals and ethylphenyl radicals; and aralkyl radicals, such as the benzyl radical and the α- and the β-phenylethyl radical.

Examples of substituted radicals R are halogenoalkyl radicals, such as the 3,3,3-trifluoro-n-propyl radical, the 2,2,2,2',2',2'-hexa-fluoroisopropyl radical and the heptafluoroisopropyl radical, and halogenoaryl radicals, such as the o-, m- and p-chlorophenyl radical, and radicals of the formula —$R^7$—[$OCH_2CH_2$]$_l$—[$OC_3H_6$]$_m$—[$O(CH_2)_4$]$_n$—OR  (VIII), in which $R^7$ is an alkylene radical having 1 to 8 carbon atoms or an arylene or aralkylene radical, 1, m and n independently of one another are 0 or an integer from 1 to 200, preferably 0 or an integer from 1 to 35, and R has a meaning given above for $R^8$.

Examples of radicals R of the formula (VIII) are
—$(CH_2)_3$—$(OCH_2CH_2)_3$—$OCH_3$, —$(CH_2)_3$—$(OCH_2CH_2)_6$—$OCH_3$,
$(CH_2)_3$—$(OCH_2CH_2)_{35}$—$OCH_3$,
—$(CH_2)_3$—$(OCH(CH_2)CH_2)_3$—$OCH_3$, —$(CH_2)_3$—$(OCH(CH_3)CH_2)_6$—$OCH_3$,
—$(CH_2)_3$—$(OCH(CH_3)CH_2)_{35}$—$OCH_3$,
—$(CH_2)_3$—$(OCH_2CH_2)_3$—$(OCH(CH_3)CH_2)_3$—$OCH_3$,
—$(CH_2)_3$—$(OCH_2CH_2)_6$—$(OCH(CH_3)CH_2)_6$—$OCH_3$,
—$(CH_2)_3$—$(OCH_2CH_2)_{35}$—$(OCH(CH_3)CH_2)_{35}$—$OCH_3$,
—$(CH_2)_3$—$(OCH_2CH_2)_3$—$OSi(CH_3)_3$, —$(CH_2)_3$—$(OCH_2CH_2)_6$—$OSi(CH_3)_3$,
—$(CH_2)_3$—$(OCH_2CH_2)_{35}$—$OSi(CH_3)_3$,
—$(CH_2)_3$—$(OCH_2CH_2)_3$—$OC(O)CH_3$, —$(CH_2)_3$—$(OCH_2CH_2)_6$—$OC(O)CH_3$,
—$(CH_2)_3$—$(OCH_2CH_2)_{35}$—$OC(O)CH_3$, —$(CH_2)_3$—$(OCH_2CH_2)_3$—OH,
—$(CH_2)_3$—$(OCH_2CH_2)_6$—OH, —$(CH_2)_3$—$(OCH_2CH_2)_{35}$—OH,
—$(CH_2)_3$—$(OCH(CH_3)CH_2)_3$—OH, —$(CH_2)_3$—$(OCH(CH_3)CH_2)_6$—OH,
—$(CH_2)_3$—$(OCH(CH_3)CH_2)_{35}$—OH,
—$(CH_2)_3$—$(OCH_2CH_2)_3$—$(OCH(CH_3)CH_2)_3$—OH,
—$(CH_2)_3$—$(OCH_2CH_2)_6$—$(OCH(CH_3)CH_2)_6$—OH,
—$(CH_2)_3$—$(OCH_2CH_2)_{35}$—$(OCH(CH_3)CH_2)_{35}$—OH and
—$(CH_2)_3$—$(OCH_2CH_2)_{18}$—$(O(CH_2)_4)_{18}$—OH.

The radical R is preferably the methyl, ethyl, or phenyl radical, the methyl radical being particularly preferred.

Examples of the radical $R^1$ are the examples mentioned for the radical R as alkyl radicals and the methoxyethyl and ethoxyethyl radical, the radical $R^1$ preferably being alkyl radicals having 1 to 4 carbon atoms, which can be interrupted by oxygen atoms, particularly preferably the methyl and the ethyl radical.

Examples of the radical $R^2$ are linear or branched alkylene radicals, such as, for example, the 1,2-ethylene, 1,3-propylene, 1,2-propylene, 1,3-(2-methylpropylene) and dimethylmethylene radical and —$CH_2$—CH=CH— and —$C(CH_3)$=CH—.

The radical $R^2$ is preferably the 1,3-propylene and 1,2-propylene radical and —$CH_2$—CH=CH—, the 1,3-propylene radical being particularly preferred.

Examples of radicals $R^3$ of the formula (VII) are
—$(CH_2CH_2O)_3$—$CH_3$, —$(CH_2CH_2O)_6$—$CH_3$,
—$(CH_2CH_2O)_{35}$—$CH_3$,
—$CH(CH_3)CH_2O)_3$—$CH_3$, —$(CH(CH_3)CH_2O)_6$—$CH_3$,
—$(CH(CH_3)CH_2O)_{35}$—$CH_3$, —$(CH_2CH_2O)_3$—$(CH(CH_3)CH_2O)_3$—$CH_3$,
$(CH_2CH_2O)_5$—$(CH_2$—$CH(CH_3)O)_5$—$CH_3$,
$(CH_2CH_2O)_{10}$—$(CH_2$—$CH(CH_3)O)_{10}$—$CH_3$,
$(CH_2CH_2O)_3$—$Si(CH_3)_3$, —$(CH_2CH_2O)_6$—$Si(CH_3)_3$,
—$(CH_2CH_2O)_{35}$—$Si(CH_3)_3$, $(CH_2CH_2O)_5$—$(CH_2$—$CH(CH_3)O)_5$—$Si(CH_3)_3$,
—$(CH_2CH_2O)_{10}$—$(CH_2$—$CH(CH_3)O)_{10}$—$Si(CH_3)_3$,
—$(CH_2CH_2O)_3$—$C(O)CH_3$, —$(CH_2CH_2O)_6$—$C(O)CH_3$,
—$(CH_2CH_2O)_{35}$—$C(O)CH_3$,
—$(CH_2CH_2O)_5$—$(CH_2$—$CH(CH_3)O)_5$—$C(O)CH_3$,
—$(CH_2CH_2O)_{10}$—$(CH_2$—$CH(CH_3)O)_{10}$—C(O)$CH_3$,
—$(CH_2CH_2O)_3$—H, —$(CH_2CH_2O)_6$—H, —$(CH_2CH_2O)_{35}$—H,
—$(CH(CH_3)CH_2O)_3$—H, —$(CH(CH_3)CH_2O)_6$—H,
—$(CH(CH_3)CH_2O)_{35}$—H, —$(CH_2CH_2O)_3$—$(CH(CH_3)CH_2O)_3$—H,
—$(CH_2CH_2O)_5$—$(CH_2$—$CH(CH_3)O)_5$—H, —$(CH_2CH_2O)_{10}$—$(CH_2$—$CH(CH_3)O)_{10}$—H
and —$(CH_2CH_2O)_{18}$—$((CH_2)_4O)_{18}$—H.

The radical $R^3$ is preferably —$(CH_2CH_2O)_6$—H, —$(CH(CH_3)CH_2O)_6$—H, —$(CH_2CH_2O)_5$—$(CH_2$—$CH(CH_3)O)_5$—H and —$(CH_2CH_2O)_{10}$—$(CH_2$—$CH(CH_3)O)_{10}$—H, where —$(CH_2CH_2O)_5$—$(CH_2$—$CH(CH_3)O)_5$—H and —$(CH_2CH_2O)_{10}$—$(CH_2$—$CH(CH_3)O)_{10}$—H are particularly preferred.

Examples of the radicals $R^4$ and $R^6$ are, independently of one another, the hydrogen atom and the examples of linear and branched alkyl radicals having 1 to 8 carbon atoms given for the radical R. The radicals $R^4$ and $R^6$ independently of one another are preferably the hydrogen atom and methyl and ethyl radical, the hydrogen atom being particularly preferred.

Examples of the radical $R^5$ are —CH=$CH_2$, —$C(CH_3)$=$CH_2$, —C≡CH, —C≡C—$CH_3$, —C≡C—$C_2H_5$, —CH=CH—$CH_3$ and —CH=$C(CH_3)_2$ where —CH=$CH_2$ and —C≡CH are preferred and —CH=$CH_2$ is particularly preferred.

Examples of radicals $R^7$ are linear or branched alkylene radicals, such as, for example, the methylene, 1,2-ethylene, 1,3-propylene and 1,2-propylene radical, where the 1,3-propylene and the 1,2-propylene radical are preferred and the 1,3-propylene radical is particularly preferred.

Examples of the radical $R^8$ are the hydrogen atom and the examples of alkyl radicals having 1 to 22 carbon atoms given for the radical R, as well as —Si(CH$_3$)$_3$ and —C(O)—CH$_3$, the hydrogen atom and the methyl and n-butyl radical being preferred.

Examples of radicals $R^9$ are the examples given for the radical R as alkyl radicals having 1 to 8 carbon atoms, the methyl radical being preferred.

Examples of the radical R are the examples given for $R^8$, where the hydrogen atom and methyl and n-butyl radicals are preferred and the hydrogen atom and methyl radical are particularly preferred.

a is preferably 1, 2 or 3.
b is preferably 0 or 1.
c is preferably 2.
o is preferably 0 or an integer from 1 to 15.
p is preferably 0 or an integer from 1 to 15.
q is preferably 0.
l is preferably 0 or an integer from 1 to 15.
m is preferably 0 or an integer from 1 to 15.
n is preferably 0.

Examples of radicals A are
—(CH$_2$)$_3$—N(R$^3$)—CH$_2$—CH=CH$_2$,
—(CH$_2$)$_3$—N(R$^3$)—H,
—(CH$_2$)$_3$—N(R$^3$)—CH$_3$,
—(CH$_2$—CH(CH$_3$)—CH$_2$)—N(R$^3$)—CH$_2$—C(CH$_3$)=CH$_2$,
—(CH$_2$—CH(CH$_3$)—CH$_2$)—N(R$^3$)—H,
—(CH=CH—CH$_2$)—N(R$^3$)—CH$_2$—C≡CH and
—(CH=CH—CH$_2$)—N(R$^3$)—H, in which $R^3$ has the abovementioned meaning.

Examples of radicals $A^1$ are
—(CH$_2$)$_3$—N(R$^3$)—(CH$_2$)$_3$—,
—(CH$_2$)$_3$—N(R$^3$)—(CH$_2$—CH=CH)—,
—(CH$_2$—CH(CH$_3$)—CH$_2$)—N(R$^3$)—CH$_2$—CH(CH$_3$)—CH$_2$— and
—(CH=CH—CH$_2$)—N(R$^3$)—(CH$_2$—CH=CH)—, in which $R^3$ has the abovementioned meaning.

The radical A is preferably —(CH$_2$)$_3$—N(R$^3$)—CH$_2$—CH=CH$_2$ and —(CH=CH—CH$_2$)—N(R$^3$)—CH$_2$—C≡CH, where —(CH$_2$)$_3$—N(R$^3$)—CH$_2$—CH=CH$_2$ is particularly preferred, and where $R^3$ has the abovementioned meaning.

The radical $A^1$ is preferably —(CH$_2$)$_3$—N(R$^3$)—(CH$_2$)$_3$— and —(CH=CH—CH$_2$)—N(R$^3$)—(CH$_2$—CH=CH)—, where —(CH$_2$)$_3$—N(R$^3$)—(CH$_2$)$_3$— is particularly preferred and where $R^3$ has the abovementioned meaning.

Examples of the organosilicon compounds according to the invention are those which are built up from the following units:

a) Me$_2$SiO$_{2/2}$, Me$_3$SiO$_{1/2}$, $_{2/2}$OMeSi—(CH$_2$)$_3$—N(R$^3$)—(CH$_2$)$_3$—SiMeO$_{2/2}$ and $_{2/2}$OMeSi—(CH$_2$)$_3$—N(R$^3$)—CH$_2$—CH=CH$_2$ and b) Me$_2$SiO$_{2/2}$, $_{1/2}$OMe$_2$Si—(CH$_2$)$_3$—N(R$^3$)—(CH$_2$)$_3$—SiMe$_2$O$_{1/2}$ and $_{1/2}$OMe$_2$Si—(CH$_2$)$_3$—N(R$^3$)—CH$_2$—CH=CH$_2$, in which $R^3$ has the abovementioned meaning.

The invention also relates to a process for the preparation of organosilicon compounds with amino-alkylene oxide functional groups, which comprises reacting organosilicon compounds of units of the general formula

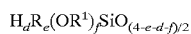   (IX), in which
R and $R^1$ have the meaning given above for these radicals,
d is 0 or 1, and is on average 0.001 to 1,
e and f independently of one another are 0, 1, 2 or 3, with the proviso that the sum d+e+f≦3 and the organosilicon compound contains more than one Si-bonded hydrogen atom, with one or more amines of the general formula

in which z, $R^3$, $R^4$ and $R^5$ have the abovementioned meaning, with the proviso that the amines according to formula (X) have at least one radical $R^5$ which differs from a hydrogen atom and at least one amine of the formula (X) where z=0 is present, in the presence of a catalyst which promotes the addition of Si-bonded hydrogen onto an aliphatic carbon—carbon multiple bond.

The organosilicon compounds employed according to the invention which have more than one Si-bonded hydrogen and comprise units of the formula (IX) have a content of Si-bonded hydrogen of preferably at least 0.04 percent by weight, particularly preferably 0.1 to 1.6 percent by weight.

The organosilicon compounds employed according to the invention which have more than one Si-bonded hydrogen and comprise units of the formula (IX) have an average viscosity of preferably 5 to 20,000 mm$^2$/s, particularly preferably 10 to 5000 mm$^2$/s, in particular from 10 to 2000 mm$^2$/s, in each case at 25° C.

Organosilicon compounds having more than one Si-bonded hydrogen atom per molecule which are preferably used in the process according to the invention are those of the formula

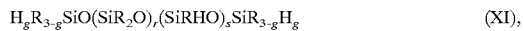   (XI), in which
R has the meaning given above for this radical,
g is 0 or 1,
r is 0 or an integer from 1 to 1500, preferably 1 to 500, and
s is 0 or an integer from 1 to 200, preferably 1 to 100, with the proviso that the organosilicon compounds contain more than one Si-bonded hydrogen atom per molecule and the r units —(SiR$_2$)O— and the s units —(SiRHO)— can be distributed as desired in the molecule.

Examples of the organosilicon compounds employed according to the invention which have more than one Si-bonded hydrogen atom per molecule are α,ω-trimethylsilyl-terminated dimethyl/methylhydrogenpolysiloxane, α,ω-dimethylhydrogensilyl-terminated dimethylpolysiloxane and α,ω-dimethylhydrogensilyl-terminated dimethyl/methylhydrogenpolysiloxane having a content of Si-bonded hydrogen of 0.1 to 1.6 percent by weight.

The organosilicon compounds employed according to the invention which have more than one Si-bonded hydrogen atom are commercially available products or can be prepared by processes known in silicon chemistry.

Examples of the amines of the formula (X) employed according to the invention are $R^3$N—(CH$_2$—CH=CH$_2$)$_2$, $R^3$N—(CH$_2$—C≡CH)$_2$, $R^3$N(H)—CH$_2$—CH=CH$_2$, H$_2$C=CH—CH$_2$—N(R$^3$)—CH$_3$, H$_2$C=CH—CH$_2$—N(R$^3$)—CH$_2$—C≡CH, H$_2$C=CH(CH$_3$)—CH$_2$—N(R$^3$)—CH$_2$—C(CH$_3$)=CH$_2$, H$_2$C=CH(CH$_3$)—CH$_2$—N(R$^3$)—H, HC≡CH—CH$_2$—N(R$^3$)—CH$_2$—C≡CH and HC≡CH—CH$_2$—N(R$^3$)—H, where the radicals R$^3$N—(CH$_2$—

$CH=CH_2)_2$, $R^3N(H)—CH_2—CH=CH_2$, $H_2C=CH—CH_2—N(R^3)—CH_3$, $HC\equiv C—CH_2—N(R^3)—CH_2—C\equiv CH$ and $H_2C=CH(CH_3)—CH_2—N(R^3)—H$ are preferred and $R^3N—(CH_2—CH=CH_2)_2$ and $R^3N—(CH_2—C\equiv CH)_2$ are particularly preferred, where $R^3$ has the abovementioned meaning.

The amines of the formula (X) employed according to the invention are commercially available products or can be prepared by processes known in organic chemistry.

The amine of the formula (X) is preferably employed in the process according to the invention in amounts such that 0.01 to 10 mol, preferably 0.1 to 5 mol of amine are present per gram atom of Si-bonded hydrogen in the organosilicon compound of units of the formula (IX).

Catalysts which promote the addition of Si-bonded hydrogen onto an aliphatic multiple bond and which can be employed in the process according to the invention are also the same catalysts which it has also hitherto been possible to employ for promoting the addition of Si-bonded hydrogen onto an aliphatic multiple bond. The catalysts are preferably a metal from the group consisting of platinum metals or a compound or a complex from the group consisting of platinum metals. Examples of such catalysts are metallic and finely divided platinum, which can be on supports, such as silicon dioxide, aluminum oxide or active charcoal, and compounds or complexes of platinum, such as platinum halides, for example $PtCl_4$, $H_2PtCl_6.6H_2O$ and $Na_2PtCl_6.4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6.6H_2O$ and cyclohexanone, platinum-vinylsiloxane complexes, such as platinum-1,3-divinyl-1,1,3,3-tetramethyldisiloxane complexes with or without a content of detectable inorganically bonded halogen, bis-($\gamma$-picoline) platinum dichloride, trimethylenedipyridineplatinum dichloride, dicyclopentadieneplatinum dichloride, dimethyl sulfoxide-ethyleneplatinum(II) dichloride, cyclooctadiene-platinum dichloride, norbornadiene-platinum dichloride, $\gamma$-picoline-platinum dichloride, cyclopentadiene-platinum dichloride and reaction products of platinum tetrachloride with olefin and primary amine or secondary amine or primary and secondary amine, such as the reaction product of platinum tetrachloride dissolved in 1-octene with sec-butylamine, or ammonium-platinum complexes. Compounds and complexes of rhodium, such as rhodium complexes, can furthermore be used as the catalysts which promote hydrosilylation.

The catalyst is preferably employed in the process according to the invention in amounts of 2 to 300 ppm by weight (part by weight per million parts by weight), particularly preferably in amounts of 5 to 100 ppm by weight, in each case calculated as elemental platinum and based on the total weight of amine of the formula (X) employed and organosilicon compound, containing Si-bonded hydrogen, of units of the formula (IX).

The process according to the invention is preferably carried out under the pressure of the ambient atmosphere, that is to say between 900 hPa and 1020 hPa; however, it can also be carried out under higher or lower pressures. The reaction generally takes place at temperatures of 25° C. to 150° C., preferably 100° C. to 130° C.

Organic solvents which are inert toward the reaction according to the invention can be co-used in the process according to the invention, but this is not preferred. Examples of such inert, organic solvents are toluene, xylene, isophorone, octane isomers, butyl acetate and isopropanol.

The process according to the invention can also be carried out in emulsion, and may be carried out continuously or discontinuously.

When the reaction according to the invention has ended, the resulting organosilicon compound containing amino groups can be isolated by known processes, for example, by removal, preferably by distillation, of the organic solvent co-used.

By the process according to the invention, organosilicon compounds having more than one Si-bonded hydrogen atom can be reacted with amines containing an aliphatic carbon—carbon multiple bond at a low temperature via the further aliphatically unsaturated groups remaining on the amine and without inhibition of the catalyst in a polymer-analogous manner, with short reaction times, without marked discoloration, and with high conversions. The reaction conditions chosen allow, for example, the preparation of siloxane copolymers carrying allyl, methallyl and propargyl groups.

The process according to the invention has the advantages that an organosilicon compound can be functionalized with amino and alkylene oxide radicals in one reaction step, it being possible for a terminal or side chain functionalization and the incorporation of the amino-alkylene oxide functions into the organosilicon chain to take place. Another advantage is the simple procedure for the process according to the invention, which leads to a complete conversion. The possibility of establishing the viscosity of the product by a controlled build-up of the chain is also a decisive advantage.

The process according to the invention has the further advantage, that by the choice and stoichiometry of the precursors, with otherwise approximately the same reaction parameters, the hydrophilicity and the amine number of the products can also be varied very easily, in addition to the viscosity.

If desired, the organosilicon compounds containing amino-alkylene oxide groups and obtained by the process according to the invention can be protonated, acylated or quaternized.

If desired, the organosilicon compounds with amino-alkylene oxide functional groups which are obtained by the process according to the invention can be equilibrated with organopolysiloxanes (1), preferably chosen from the group consisting of linear organopolysiloxanes containing terminal triorganosiloxy groups, linear organopolysiloxanes containing terminal hydroxyl groups, cyclic organopolysiloxanes and copolymers of diorganosiloxane and monoorganosiloxane units, as a result of which, for example, it becomes possible to establish the desired molecular weight and to distribute the amino groups in the molecule in a controlled manner.

Preferably, linear organopolysiloxanes containing terminal triorganosiloxy groups which are employed are those of the formula $$R^{10}{}_3SiO(SiR^{10}{}_2O)_uSiR^{10}{}_3 \tag{XII},$$

linear organopolysiloxanes containing terminal hydroxyl groups which are employed are those of the formula $$HO(SiR^{10}{}_2O)_vH \tag{XIII},$$

cyclic organopolysiloxanes which are employed are those of the formula $$(SiR^{10}{}_2O)_t \tag{XIV},$$

and copolymers which are employed are those of units of the formula $R^{10}{}_3SiO_{1/2}$, $R^{10}{}_2SiO$, and $R^{10}SiO_{3/2}$, in which $R^{10}$ in each case can be identical or different and has a meaning given for R, u is 0 or an integer from 1 to 1500, v is 0 or an integer from 1 to 1500 and t is an integer having a value from 3 to 12.

The ratios of the amounts of the organopolysiloxanes (1) employed in the optional equilibration and the organosilicon compounds with amino-alkylene oxide functional groups prepared according to the invention, are determined merely by the desired content of amino-alkylene oxide groups in the organopolysiloxanes produced in the optional equilibration out and by the desired average chain length.

Basic catalysts which promote the equilibration are preferably employed in the equilibration. Examples of such catalysts are benzyltrimethyl-ammonium hydroxide, tetramethylammonium hydroxide, alkali metal hydroxide(s) and alkaline earth metal hydroxide(s) in methanolic solution, and silanolates. Alkali metal hydroxides are preferred here, and are used in amounts of preferably 50 ppm to 10,000 ppm (parts per million) by weight, in particular 500 ppm to 2000 ppm by weight, in each case based on the total weight of the organosilicon compounds employed.

The equilibration optionally carried out is preferably carried out at 80° C. to 150° C. under the pressure of the ambient atmosphere, that is to say between 900 hPa and 1100 hPa. However, it can also be carried out under higher or lower pressures.

If desired, the equilibration can be carried out in a solvent which is not miscible with water, such as toluene, but this is not preferred. If such organic solvents are employed, however, amounts of 5 to 20 percent by weight, based on the total weight of the organosilicon compounds employed, are preferred.

The catalyst can be rendered inactive before working up of the mixture obtained in the equilibration according to the invention.

The organosilicon compounds with amino-alkylene oxide functional groups according to the invention or prepared according to the invention are distinguished by transparency, low discoloration, and absence of odor.

The possibility of establishing hydrophilicity and amine number in a controlled manner, which is possible independently of one another, represents a further advantage of the organosilicon compounds according to the invention.

Another advantage of the organosilicon compounds with amino-alkylene oxide functional groups according to the invention or prepared according to the invention which contain OH-terminated alkylene oxide functions is the extremely low content of Si—OC linkages in the polymer, which has a positive effect on the long-term stability of the products.

The organosilicon compounds containing amino-alkylene oxide groups according to the invention or prepared according to the invention or, if appropriate, the siloxane copolymers with optionally partly or completely protonated or partly or completely quaternized amino groups can be applied, for example as a constituent of an emulsion, to textiles of all types, such as, for example, to cotton, synthetic fibers or, for example, leather, and lead to a hydrophilic treatment of these fabrics with, if appropriate, a desired soft handle.

The organosilicon compounds according to the invention or prepared according to the invention which contain alkenyl groups, that is to say those where z is 1 and $R^5$ is other than hydrogen, also have the advantage that they can be crosslinked with compounds with Si-bonded hydrogen by further hydrosilylation reactions in a controlled manner.

The organosilicon compounds containing amino groups according to the invention or prepared according to the invention can be employed for all purposes for which organosilicon compounds with amino groups or aliphatically unsaturated radicals have also hitherto been used, such as, for example, in cosmetics and antifoam applications, for textile treatment, fiber treatment, for carpets, leather treatment, for so-called polish, in addition-crosslinkable systems, such as paper coatings or as permanent fabric coatings, and in rubbers.

The organosilicon compounds according to the invention or prepared according to the invention can thus be used, for example, in compositions, in particular emulsions, for treatment of organic fibers of all types, such as, for example, textiles of cotton and/or synthetic fibers, or leather, such compositions according to the invention usually leading to a permanent, hydrophilic treatment of the materials mentioned with, if appropriate, the desired soft handle.

When used in textile treatment, the organosilicon compounds according to the invention or prepared according to the invention have the advantage that the textiles treated with these show little yellowing, a very high hydrophilicity and a very good soft handle.

In the following examples, all the parts and percentages data relate to the weight, unless stated otherwise. Unless stated otherwise, the following examples are carried out under a pressure of the ambient atmosphere, that is to say under about 1000 hPa, and at room temperature, that is to say at about 20° C., or at a temperature which is established when the reactants are brought together at room temperature without additional heating or cooling. All the viscosity data stated in the examples are intended to relate to a temperature of 25° C.

In the following examples, the number which indicates the amount of iodine consumed during addition onto the aliphatic multiple bond in grams per 100 grams of material employed which is to be analyzed is designated the iodine number.

EXAMPLE 1

15.4 g of an ethoxylated/propoxylated diallylamine (20.0 mmol) having on average 5 propoxy and 5 ethoxy units and a molecular weight $M_w$ of 768 g/mol, of the average formula

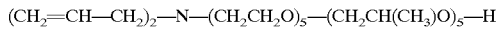

$(CH_2=CH—CH_2)_2—N—(CH_2CH_2O)_5—(CH_2CH(CH_3)O)_5—H$ are initially introduced into the reaction vessel under inert nitrogen conditions and are heated up to 120° C. 320 μl (50 ppm) of an acetylacetonyl-cyclooctenyl-platinum(II) acetylacetonate catalyst in isobutyl methyl ketone (1% strength solution) are added at this temperature. 40.6 g (20.0 mmol of Si—H) of an α,ω-dihydrogenpolydimethylsiloxane of average chain length 55 and having a viscosity of 67 mm²/s are then metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil with a viscosity of 834 mm²/s and an iodine number of 9.74 is obtained. The yield is 97%.

EXAMPLE 2

In a 1st Stage, 50.0 g of the ethoxylated/propoxylated diallylamine (65.1 mmol) described in Example 1 are stirred with 7.14 g (70.0 mmol) of acetic anhydride and one drop of concentrated sulfuric acid at 80° C. for 1 hour. After removal of volatile constituents at 110° C. under a pressure of 5 mbar, the mixture is neutralized with sodium bicarbonate and filtered. A clear oil with a viscosity of 70.6 mm²/s and an iodine number of 52.8 is obtained. The yield is 95%.

In a 2nd Stage, 16.7 g of the ethoxylated/propoxylated diallylamine (20.6 mmol) terminated with acetyl groups and which is obtained in the first stage (on average 5 propoxy and 5 ethoxy units, molecular weight $M_w$=810 g/mol) are initially introduced into the reaction vessel under inert nitrogen conditions and are heated up to 120° C. 320 µl (50 ppm) of an acetylacetonyl-cyclooctenyl-platinum(II) acetylacetonate catalyst in isobutyl methyl ketone (1% strength solution) are added at this temperature. 40.6 g (20.0 mmol of Si—H) of an α,ω-dihydrogenpolydimethylsiloxane of average chain length 55 and having a viscosity of 67 mm²/s are then metered in over a period of 60 minutes and the reaction mixture is kept at a temperature of 120° C. for 2 hours. Thereafter, the volatile constituents are removed at 110° C. under a pressure of 5 mbar. After cooling and subsequent filtration, a clear, pale yellow oil with a viscosity of 928 mm²/s and an iodine number of 9.48 is obtained. The yield is 96%.

EXAMPLE 3

25.1 g of an ethoxylated/propoxylated diallylamine (20.0 mmol) having on average 10 propoxy and 10 ethoxy units and a molecular weight $M_w$ of 1256 g/mol, of the average formula

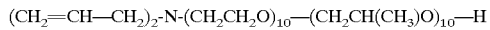

$(CH_2=CH-CH_2)_2-N-(CH_2CH_2O)_{10}-(CH_2CH(CH_3)O)_{10}-H$ are initially introduced into the reaction vessel under inert nitrogen conditions and are heated up to 120° C. 370 µl (50 ppm) of an acetylacetonyl-cyclooctenyl-platinum(II) acetylacetonate catalyst in isobutyl methyl ketone (1% strength solution) are added at this temperature. 40.6 g (20.0 mmol of Si—H) of an α,ω-dihydrogenpolydimethylsiloxane of average chain length 55 and having a viscosity of 67 mm²/s are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil having a viscosity of 5916 mm²/s and an iodine number of 6.89 is obtained. The yield is 97%.

EXAMPLE 4

50.2 g of the ethoxylated/propoxylated diallylamine (40.0 mmol) described in Example 3 are initially introduced into 65.6 g of toluene under inert nitrogen conditions and the mixture is heated up to 120° C. 740 µl (50 ppm) of an acetylacetonyl-cyclooctenyl-platinum(II) acetylacetonate catalyst in isobutyl methyl ketone (1% strength solution) are added at this temperature. 81.2 g (40.0 mmol of Si—H) of an α,ω-di-hydrogenpolydimethylsiloxane of average chain length 55 and having a viscosity of 67 mm²/s are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil with a viscosity of 5916 mm²/s and an iodine number of 6.89 is obtained. The yield is 94%.

EXAMPLE 5

37.6 g of the ethoxylated/propoxylated diallylamine (30.0 mmol) described in Example 3 are initially introduced into 50.9 g of toluene under inert nitrogen conditions and the mixture is heated up to 120° C. 804 µl (50 ppm) of an acetylacetonyl-cyclooctenyl-platinum(II) acetylacetonate catalyst in isobutyl methyl ketone (1% strength solution) are added at this temperature. 104.2 g (51.0 mmol of Si—H) of an α,ω-di-hydrogenpolydimethylsiloxane of average chain length 55 and having a viscosity of 67 mm²/s are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil with a viscosity of 36,200 mm²/s and an iodine number of 1.87 is obtained. The yield is 95%.

EXAMPLE 6

24.0 g of the ethoxylated/propoxylated diallylamine (32.0 mmol) described in Example 1 are initially introduced into 21.1 g of toluene under inert nitrogen conditions and the mixture is heated up to 120° C. 694 µl (50 ppm) of an acetylacetonyl-cyclooctenyl-platinum(II) acetylacetonate catalyst in isobutyl methyl ketone (1% strength solution) are added at this temperature. 98.2 g (48.0 mmol of Si—H) of an α,ω-di-hydrogenpolydimethylsiloxane of average chain length 55 and having a viscosity of 67 mm²/s are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil with a viscosity of 26,700 mm²/s and an iodine number of 2.06 is obtained. The yield is 98%.

EXAMPLE 7

100.6 g of the ethoxylated/propoxylated diallylamine (80.0 mmol) described in Example 3 are initially introduced into 51.2 g of toluene under inert nitrogen conditions and the mixture is heated up to 120° C. 698 µl (50 ppm) of an acetylacetonyl-cyclooctenyl-platinum(II) acetylacetonate catalyst in isobutyl methyl ketone (1% strength solution) are added at this temperature. 22.4 g (76.2 mmol of Si—H) of an α,ω-dihydrogenpolydimethylsiloxane having a viscosity of 3.5 mm²/s and of average chain length 8 are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil with a viscosity of 480 mm²/s and an iodine number of 12.82 is obtained. The yield is 94%.

EXAMPLE 8

92.2 g of the ethoxylated/propoxylated diallylamine (120.0 mmol) described in Example 1 are initially introduced into 21.4 g of toluene under inert nitrogen conditions and the mixture is heated up to 120° C. 714 µl (50 ppm) of an acetylacetonyl-cyclooctenyl-platinum(II) acetylacetonate catalyst in isobutyl methyl ketone (1% strength solution) are added at this temperature. 33.6 g (114.0 mmol of Si—H) of an α,ω-di-hydrogenpolydimethylsiloxane of average chain length 8 and having a viscosity of 3.5 mm²/s are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil with a viscosity of 204 mm²/s and an iodine number of 15.03 is obtained. The yield is 94%.

EXAMPLE 9

88.0 g of the ethoxylated/propoxylated diallylamine (70.0 mmol) described in Example 3 are initially introduced into 51.0 g of toluene under inert nitrogen conditions and the mixture is heated up to 120° C. 752 μl (50 ppm) of an acetylacetonyl-cyclooctenyl-platinum(II) acetylacetonate catalyst in isobutyl methyl ketone (1% strength solution) are added at this temperature. 44.4 g (66.0 mmol of Si—H) of an α,ω(-trimethylsiloxy-dimethyl/methylhydrogensiloxane having a viscosity of 32 mm²/s are subsequently metered in over a period of 60 minutes and the reaction mixture is kept at a temperature of 120° C. for 2 hours. Thereafter, Volatile constituents are removed at 110° C. under a pressure of 5 mbar. After cooling and subsequent filtration, a clear, pale yellow oil with a viscosity of 14 million mm²/s and an iodine number of 13.3 is obtained. The yield is 96%.

EXAMPLE 10

20.0 g of the organosilicon compound prepared in Example 8 having a viscosity of 204 mm²/s and an iodine number of 15.03 and 1.75 g (28 mmol) of an α,ω-trimethylsilyl-terminated dimethyl/methylhydrogenpolysiloxane having a viscosity of 22.5 mm²/s and 124 μl of a 1.1% strength solution of acetylacetonyl-cyclooctenyl-platinum(II) acetylacetonate catalyst in isobutyl methyl ketone (50 ppm of platinum) are initially introduced into the reaction vessel at room temperature:

a) crosslinking takes place at a crosslinking temperature of 23° C. after 90 minutes.
b) crosslinking takes place at a crosslinking temperature of 50° C. after 7 minutes.

EXAMPLE 11

76.8 g of the ethoxylated/propoxylated diallylamine (100.0 mmol) described in Example 1 are initially introduced into 34.3 g of toluene under inert nitrogen conditions and the mixture is heated up to 120° C. 588 μl (50 ppm) of an acetylacetonyl-cyclooctenyl-platinum(II) acetylacetonate catalyst in isobutyl methyl ketone (1% strength solution) are added at this temperature. 26.7 g (40.0 mmol of Si—H) of an α,ω-trimethylsiloxy-dimethyl/methylhydrogensiloxane having a viscosity of 32 mm²/s are subsequently metered in over a period of 60 minutes and the reaction mixture is kept at a temperature of 120° C. for 2 hours. Thereafter, volatile constituents are removed at 110° C. under a pressure of 5 mbar. After cooling and subsequent filtration, a clear, pale yellow oil having a viscosity of 262 mm²/s and an iodine number of 36.9 is obtained. The yield is 98%.

What is claimed is:

1. An organosilicon compound with amino-alkylene oxide functional groups containing a) siloxane units of the formula $$R_aSi(OR^1)_bO_{(4-a-b)/2} \quad (I),$$

in which

R are identical or different hydrocarbon radicals having 1 to 200 carbon atoms, which are optionally substituted by halogen atoms or alkoxy or hydroxyl groups and can be interrupted by one or more oxygen atoms, $R^1$ are identical or different alkyl radicals having 1 to 8 carbon atoms, which can be interrupted by one or more oxygen atoms, a is 0, 1, 2 or 3 and b is 0, 1, 2 or 3, with the proviso that the sum a+b≦3, and b) per molecule, at least one unit of the formula $$AR_cSiO_{(4-c-1)/2} \quad (II)$$

and at least one unit of the formula $$O_{(4-c-1)/2}R_cSi-A^1-SiR_cO_{(4-c-1)/2} \quad (III),$$

in which

R are identical or different and have one of the above-mentioned meanings for R, c can be identical or different and is 0, 1 or 2, A is a radical of the formula $$-R^2N \begin{matrix} H_{1-z} \\ | \\ | \\ R^3 \end{matrix} (CR_2^4-R^5)_z \quad (IV)$$

and $A^1$ is a radical of the formula $$-R^2N \begin{matrix} \\ | \\ R^3 \end{matrix} -R^2-, \quad (VI)$$

in which $R^2$ are identical or different and are divalent hydrocarbon radicals having 2 to 12 carbon atoms, $R^3$ are identical or different and are radicals of the general formula $$-[CH_2CH_2O]_o-[C_3H_6O]_p-[(CH_2)_4O]_q-R^8 \quad (VII),$$

in which $R^8$ is a hydrogen atom, an alkyl radical having 1 to 22 carbon atoms, a group of the formula $-SiR_x(OR^1)_y$, in which R and $R^1$ can be identical or different and have one of the abovementioned meanings and x and y independently of one another are 0, 1, 2 or 3, with the proviso that x+y equals 3, or is a radical of the formula $-CO-R^9$, where $R^9$ is an alkyl radical having 1 to 8 carbon atoms, z is 0 or 1 and o, p and q independently of one another are 0 or an integer from 1 to 200, with the proviso that the sum o+p+q>0, $R^4$ are identical or different and are a hydrogen atom or an alkyl radical having 1 to 8 carbon atoms and $R^5$ are a hydrogen atom or a radical of the formula $-CR^6=CR^6_2$ or $-C\equiv CR^6$, in which $R^6$ can be identical or different and are a hydrogen atom or an alkyl radical having 1 to 8 carbon atoms.

2. An organosilicon compound containing amino-alkylene oxide functional groups as claimed in claim 1, which has an amine number of 0.003 to 6.

3. An organosilicon compound with amino-alkylene oxide functional groups as claimed in claim 1, in which $R^3$ is $-(CH_2CH_2O)_5-(CH_2-CH(CH_3)O)_5-H$ or $-(CH_2CH_2O)_{10}-(CH_2-CH(CH_3)O)_{10}-H$.

4. An organosilicon compound of claim 1 wherein c is 2.

5. An organosilicon compound of claim 1, wherein o, p, and q independently are 0 or an integer from 1 to 35.

6. A process for the preparation of an organosilicon compound with amino-alkylene oxide functional groups, which comprises reacting an organosilicon compound of units of the general formula $$H_d R_e (OR^1)_f SiO_{(4-e-d-f)/2} \quad (IX),$$

in which

R are identical or different hydrocarbon radicals having 1 to 200 carbon atoms, which are optionally substituted by halogen atoms or alkoxy or hydroxyl groups and can be interrupted by one or more oxygen atoms, $R^1$ are identical or different alkyl radicals having 1 to 8 carbon atoms, which can be interrupted by one or more oxygen atoms, d is 0 or 1, and is on average 0.001 to 1, e and f independently of one another are 0, 1, 2 or 3, with the proviso that the sum $d+e+f \leq 3$ and the organosilicon compound contains more than one Si-bonded hydrogen atom, with one or more amines of the general formula $$R^3 N(\!\!-\!\!CR_2^4\!\!-\!\!R^5)_{2-z} \overset{H_z}{|} \quad (X)$$

in which z is 0 or 1, $R^3$ are identical or different and are radicals of the general formula $$-[CH_2CH_2O]_o-[C_3H_6O]_p-[(CH_2)_4O]_q-R^8 \quad (VII),$$

in which $R^8$ is a hydrogen atom, an alkyl radical having 1 to 22 carbon atoms, a group of the formula $-SiR_x(OR^1)_y$, in which R and $R^1$ can be identical or different and have one of the abovementioned meanings and x and y independently of one another are 0, 1, 2 or 3, with the proviso that x+y equals 3, or is a radical of the formula $-CO-R^9$, where $R^9$ is an alkyl radical having 1 to 8 carbon atoms, $R^4$ are identical or different and are a hydrogen atom or an alkyl radical having 1 to 8 carbon atoms and $R^5$ are a hydrogen atom or a radical of the formula $-CR^6=CR^6_2$ or $-C\equiv CR^6$, in which $R^6$ can be identical or different and are a hydrogen atom or an alkyl radical having 1 to 8 carbon atoms, with the proviso that the amines according to formula (X) have at least one radical $R^5$ which differs from a hydrogen atom and at least one amine of the formula (X) where z=0 is present, in the presence of a catalyst which promotes the addition of Si-bonded hydrogen onto an aliphatic carbon—carbon multiple bond.

7. The process as claimed in claim 6, wherein the organosilicon compound with more than one Si-bonded hydrogen atom per molecule is preferably one of the formula $$H_g R_{3-g} SiO(SiR_2O)_r (SiRHO)_s SiR_{3-g} H_g \quad (XI),$$

in which

R has the meaning given above for this radical, g is 0 or 1, r is 0 or an integer from 1 to 1500 and s is 0 or an integer from 1 to 200, with the proviso that the organosilicon compounds contain more than one Si-bonded hydrogen atom per molecule and the r units $-(SiR_2)O-$ and the s units $-(SiRHO)-$ can be distributed as desired in the molecule.

8. The process as claimed in claim 6, wherein the amine of the formula (X) is employed in amounts such that 0.01 to 10 mol of amine are present per gram atom of Si-bonded hydrogen in the organosilicon compound of units of the formula (IX).

9. The process as claimed in claim 7, wherein the amine of the formula (X) is employed in amounts such that 0.01 to 10 mol of amine are present per gram atom of Si-bonded hydrogen in the organosilicon compound of units of the formula (IX).

* * * * *